US008652422B2

(12) United States Patent
Mabuchi et al.

(10) Patent No.: US 8,652,422 B2
(45) **Date of Patent: *Feb. 18, 2014**

(54) IMMUNOASSAY PRODUCT AND PROCESS

(75) Inventors: Masaharu Mabuchi, Beverly, MA (US); Hiroko Kimura, Yokohama (JP); Marc Emerick, Amesbury, MA (US); Phillip Clark, Wakefield, MA (US); Kurt Greenizen, Bradford, MA (US)

(73) Assignee: EMD Mllipore Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/078,290

(22) Filed: Apr. 1, 2011

(65) Prior Publication Data

US 2011/0256025 A1 Oct. 20, 2011

Related U.S. Application Data

(62) Division of application No. 11/582,599, filed on Oct. 18, 2006.

(60) Provisional application No. 60/795,452, filed on Apr. 27, 2006, provisional application No. 60/795,532, filed on Apr. 27, 2006, provisional application No. 60/732,994, filed on Nov. 3, 2005.

(51) Int. Cl.
*G01N 33/50* (2006.01)
*C12M 1/40* (2006.01)

(52) U.S. Cl.
USPC .......... 422/535; 435/7.94; 422/409; 422/420; 422/430

(58) Field of Classification Search
USPC ................. 422/401, 402, 409, 420, 430, 535; 435/7.94
See application file for complete search history.

(56) References Cited

U.S. PATENT DOCUMENTS 4,427,415 A 1/1984 Cleveland
4,717,656 A 1/1988 Swanljung
(Continued)

FOREIGN PATENT DOCUMENTS

CN 1328640 A 12/2001
EP 0312394 A2 4/1989
(Continued)

OTHER PUBLICATIONS

Extended European Search Report received for EP Patent Application No. 06255512.3, mailed on Feb. 21, 2007, 5 pages.

(Continued)

*Primary Examiner* — Paul Hyun
(74) *Attorney, Agent, or Firm* — EMD Millipore Corporation

(57) ABSTRACT

The invention is directed to an apparatus useful in conducting detection of compounds on blotting membranes. The device is comprised of several layers including a porous support layer below the blotting membrane(s), a flow distributor above the blotting membrane(s) and optionally a well on the flow distributor to contain the liquid to the desired area and to allow for lower starting volumes of such liquid. Preferably, the flow distributor is a non-binding or low binding hydrophilic porous membrane such as a 0.22 micron membrane and the support layer is a grid or sintered porous material. The distributor and support are held together to form an envelope around the membrane(s). The use of a hinge, clips and other such devices is preferred in doing so.

12 Claims, 12 Drawing Sheets

(56) References Cited

U.S. PATENT DOCUMENTS

| | | | |
|---|---|---|---|
| 4,826,759 | A | 5/1989 | Guire et al. |
| 4,834,946 | A | 5/1989 | Levin |
| 4,948,442 | A | 8/1990 | Manns |
| 5,039,493 | A | 8/1991 | Oprandy |
| 5,108,704 | A | 4/1992 | Bowers et al. |
| 5,141,719 | A | 8/1992 | Fernwood et al. |
| 5,149,408 | A | 9/1992 | Perlman |
| 5,155,049 | A | 10/1992 | Kauvar et al. |
| 5,264,184 | A | 11/1993 | Aysta et al. |
| 5,368,729 | A | 11/1994 | Stefkovich et al. |
| 6,303,389 | B1 | 10/2001 | Levin et al. |
| 6,395,504 | B1 | 5/2002 | Trudil |
| 6,656,428 | B1 | 12/2003 | Clark et al. |
| 8,460,618 | B2 * | 6/2013 | Mabuchi et al. ............. 422/535 |
| 2001/0001643 | A1 | 5/2001 | Simpson et al. |
| 2002/0187089 | A1 | 12/2002 | Buxbaum |
| 2003/0143124 | A1 | 7/2003 | Roberts et al. |
| 2004/0048392 | A1 | 3/2004 | Kidd |
| 2004/0245163 | A1 | 12/2004 | Lim et al. |
| 2004/0247490 | A1 | 12/2004 | Olivier et al. |
| 2007/0111325 | A1 | 5/2007 | Van Beuningen et al. |
| 2007/0243628 | A1 | 10/2007 | Mabuchi et al. |

FOREIGN PATENT DOCUMENTS

| | | | |
|---|---|---|---|
| EP | 1151794 | B1 | 6/2006 |
| JP | 2-187110 | A | 7/1990 |
| JP | 4-227032 | A | 8/1992 |
| WO | 92/16294 | A1 | 10/1992 |
| WO | 00/20862 | A1 | 4/2000 |
| WO | 2004/013607 | A2 | 2/2004 |
| WO | 2005/003346 | A1 | 1/2005 |

OTHER PUBLICATIONS

Extended European Search Report received for EP Patent Application No. 06255513.1, mailed on Feb. 20, 2007, 5 pages.

Extended European Search Report received for EP Patent Application No. 09153124.4, mailed on Apr. 14, 2009, 6 pages.

Mabuchi et al., "Vacuum Assisted Immunoassay Product and Process", U.S. Appl. No. 60/732,994, filed on Nov. 3, 2005, 17 pages.

Biocompare, The Buyers Guide for Life, Sciences, "SNAP I.D. Protein Detection System from Millipore", Online available at <http://www.biocompare.com/Articles/ProductReview/1257/Snap-ID-Protein-Detection-System> retrieved on Sep. 20, 2013, 3 pages.

"Product Review Snap i.d. Rapid Western Blotting System", Online Available at <http://bitesizebio.com/articles/product-review-snap-i-d-rapid-western-blotting-system/>, retrieved on Sep. 20, 2013, 5 pages.

* cited by examiner

IMMUNOASSAY PRODUCT AND PROCESS

CROSS-REFERENCE TO RELATED APPLICATIONS

This application is a divisional patent application of U.S. application Ser. No.: 11/582,599, filed on Oct. 18, 2006 and claims the benefit of U.S. Provisional Application No. 60/795,452, filed on Apr. 27, 2006, U.S. Provisional Application No. 60/795,532, filed on Apr. 27, 2006 and U.S. Provisional Application No.: 60/732,994, filed on Nov. 3, 2005.

The invention relates to a device and process for the detection and position of substances that are contained in a blotting membrane. More particularly, it concerns a technique for applying reagents and wash solutions to a blotting membrane to accomplish this detection quickly via the use of vacuum or positive pressure.

BACKGROUND OF THE INVENTION

The use of gel electrophoresis is currently the ubiquitous technique for the separation of biological materials. Nonbiological materials can also be separated using gels or other chromatographic supports as well, but the scope of effort with regard to biologicals is greater. Typical applications include separation of nucleic acid fragments of various sizes either in the context of sequence determination; in the detection of polymorphisms; or verification of sizes in other contexts. Also frequently conducted are separations of proteins, glycoproteins, protein fragments and application of gel separations as verification of homogeneity or purity, identification of post translational modifications and confirmation of molecular weight.

In all of these procedures, mixed samples of biological entities are applied to electrophoretic gels and the components are separated by application of an electric field across the gel. Regardless of the manner in which the gel is developed, the resulting pattern of migration of the substances contained in the sample must be detected in some manner.

To conduct this detection, typically the gel support is contacted with a blotting membrane to which the substances are transferred in the same pattern in which they appeared on the gel. The "spots" are then detected, at a minimum, by blocking the membrane with a protein or detergent solution to reduce non-specific binding (which otherwise leads to a high level of noise and low level of detection). Typical blocking agents include casein, bovine serum albumin (BSA), non-fat dry milk (generally about 1-5%) in a Tris buffer saline solution with TWEEN® surfactant (TBS-T solution) or phosphate buffer saline solution with TWEEN® surfactant (PBS-T solution). The biological entity is then incubated with an antibody specific for the antigen on the membrane. The membrane is then extensively washed to remove any contaminants, unbound blocking proteins or antibodies and the like. The membrane is then treated and incubated with a secondary enzyme-, radioisotope-, fluorfluor-, or biotin-conjugated antibody specific for the primary antibody. The membrane is then extensively washed again to remove any unbound secondary antibody. Then a detection reagent, generally a chromogenic, chemiluminescent, fluorescent, radiological, or streptavidin-labeled material, is applied which either binds to, or is a substrate of the enzyme-conjugate. Lastly, the appropriate detection device is used to determine the presence, absence, position, quantity, etc. of the biological entity. The last six steps generally take from 3-6 hours to overnight depending on the speed of the reaction between the selected reagents, the membrane and the biological entity. The process requires multiple incubation periods of the membrane on a rocking or other suitable mixing platform. It is a lengthy process that most researchers dislike and which consumes (wastes) a large volume of reagents.

Some researchers have suggested the use of the capillary action of an absorbent material such as filter paper placed below the membrane to draw the remaining fluids through the membrane and improve the speed of the process especially the washing steps.

U.S. Pat. No. 5,155,049 mentions a system called the Hybrid-Ease™ hybridization chamber marketed by Hoefer Scientific Instruments. This chamber is comprised two grids between which the membrane is sandwiched. The grid plates are snapped into position surrounding the membrane, and syringes fitted into the open space created by the grids. One syringe is used to apply reagents and wash, and the other to withdraw excess. The system requires large volumes of liquid in order to operate, is cumbersome to employ and is still quite time consuming. It also mentions that in some particular assays, such as ELISA assays, in small volume wells (such as 96 well microtiter plate), others have used vacuum to draw liquids through a membrane in a washing step. However, they discount this effort as it is only available in small volume applications and still is uncontrollable. They suggest instead that the better method is to use a manual press having the membrane on top of a filter paper and cover layer and then pressing the membrane sandwich between two plates to squeeze the liquid through the membrane and into the paper.

In U.S. Ser. No. 60/732,994, filed Nov. 3, 2005 it is suggested that one use a device formed of several layers including a porous support layer below the one or more layers of blotting membrane, a flow distributor above the blotting membrane(s) and a well on the flow distributor to contain the liquid to the desired area and to allow for lower starting volumes of such liquid. Preferably, the flow distributor is a non-binding or low binding porous membrane such as a 0.22 micron membrane. The device layers are assembled in order and then subjected to vacuum or pressure filtration to wash and detect the biological entities on the membrane.

It is clear that a more efficient method for detection of the biological materials or entities on blotting membranes is required. The present invention permits a more effective and efficient detection of biological entities in a blotting membrane.

SUMMARY OF THE INVENTION

In one embodiment, the invention is directed to an apparatus useful in conducting the method of the invention. The device is comprised of a blotting membrane holder formed of a lower porous support layer and an upper flow distributor. The two are held together by a method such as by a hinge, clips, elastic bands, adhesives, ball and socket, pins and recesses, or cooperatively engaging fasteners or other such means. The holder is opened and one or more blotting membranes are placed between the lower and upper layers. The holder is then sealed and placed either onto a manifold or into a special apparatus (described below) to process the samples on the blotting membrane. In one embodiment, the flow distributor has an outer perimeter wall extending upwardly from the flow distributor to form a well to hold reagents and washing fluids.

In another embodiment the well and flow distributor are subdivided into two or more subwells to run parallel blotting membranes or subparts of one blotting membrane, each membrane is typically processed with at least one different reagent.

In another embodiment, the flow distributor is a non-binding or low binding porous membrane such as a 0.22 micron membrane.

In another embodiment, a porous pliable layer, such as a filter paper or glass paper, is placed below the blotting membrane and above the porous support so that when the flow distributor membrane is secured against the blotting membrane the pliable layer deforms to insure a complete mating and uniform flow between the blotting membrane and the flow distributor.

In a further embodiment the holder has an integral well formed above the flow distributor to hold reagents and/or wash fluids during the processing of them.

Additional embodiments include a pressure or vacuum manifold designed to retain the holder and conduct the filtration steps. In one embodiment, a separate well device is placed adjacent to the top of the flow distributor, either directly or through contact when the manifold lid is closed. In another, the well is integrally formed on top of the flow distributor In another embodiment a rapid, efficient and convenient method to detect one or more biological entities on a blotting membrane is provided. The detection can relate to the position, nature or amount of the biological substance on a membrane. The invention method involves a pressure assisted regiment, selected from positive pressure or a vacuum for the supply and removal of reagents to and from the blotting membrane and permits washing of the contaminants from substances embedded in the membrane that are to be detected using very low volumes of liquid and reagents. This method enables completion of the blocking, washing and antibody binding steps in about 30-45 minutes without compromising blot quality. One simply takes a holder, opens it and places the blotting membrane(s) on one of the surfaces such that the lower surface of the blotting membrane is adjacent the porous support and the upper surface of the blotting membrane is adjacent the flow distributor when the device is closed around the membrane(s). The device is placed on or in a manifold having a pressure or vacuum supply and the process is commenced.

It is an object of the present invention to provide a device for conducting pressure or vacuum assisted immunoassays comprising a holder for the one or more blotting membranes formed of a porous support and a flow distributor which are held together.

It is another object of the present invention to provide an apparatus for conducting pressure or vacuum assisted immunoassays comprising a holder for the one or more blotting membranes formed of a porous support and a flow distributor which are removably held together and the flow distributor having an upwardly extending wall from its upper surface which forms one or more reagent wells on top of the flow distributor.

It is another object of the present invention to provide a device for conducting vacuum assisted immunoassays of one or more blotting membranes comprising a vacuum manifold and a holder for the one or more blotting membranes formed of a porous support and a flow distributor which are held together.

It is another object of the present invention to provide an apparatus for conducting pressure or vacuum assisted immunoassays of one or more blots comprising a vacuum manifold and a holder for processing the blots and a mean of collecting one or more of the antibodies.

It is a further object of the present invention to provide a device for conducting positive pressure assisted immunoassays comprising a manifold, a holder for one or more blotting membranes, the holder being formed of a porous support and a flow distributor which are held together and a positive pressure device removably mounted on top of the flow distributor.

It is a further object of the present invention to provide a process for conducting vacuum assisted immunoassays on one or more membranes comprising the steps of:

a. providing a vacuum manifold, a holder for the one or more blotting membranes formed of a porous support and a flow distributor which are held together, one or more membranes containing one or more biological entities to be assayed, the membrane(s) being placed on the porous support, a flow distributor being on top of the membrane and one or more wells placed on top of the flow distributor portion of the holder,
b. adding one or more reagents to the one or more wells and applying a vacuum to pull the reagents into the membrane, and
c. adding one or more washing agents to the one or more wells and applying a vacuum to pull the washing agents and any unbound reagents through the flow distributor, membrane and porous support and into the vacuum manifold and
d. repeating steps (b and c) one or more additional times as desired or required.

It is an object of the present invention to provide a process of passing a wash or reagent-containing liquid through one or more blotting membranes containing one or more biological entities, at least one of which is to be detected wherein the process comprises:

a. providing a vacuum manifold, a holder for the one or more blotting membranes formed of a porous support and a flow distributor which are held together,
b. placing the one or more blotting membranes containing the one or more biological entities into the holder such that the lower surface of the blotting membrane(s) is adjacent the porous support and the upper surface of the blotting membrane(s) is adjacent the flow distributor when the device is closed around the membrane(s),
c. securely closing the holder, and
d. adding a liquid to the top of the flow distributor, and applying a vacuum to draw the liquid through the flow distributor, blotting membrane(s) and porous support into the manifold.

It is an object of the present invention to provide a process of passing a wash or reagent-containing liquid through one or more blotting membranes containing one or more biological entities, at least one of which is to be detected wherein the process comprises:

a. providing a manifold, a holder for the one or more blotting membranes formed of a porous support and a flow distributor which are held together,
b. placing the one or more blotting membranes containing the one or more biological entities into the holder such that the lower surface of the blotting membrane(s) is adjacent the porous support and the upper surface of the blotting membrane(s) is adjacent the flow distributor when the device is closed around the membrane(s),
c. securely closing the holder, and,
d. adding a liquid to the top of the flow distributor, and applying a positive pressure to the flow distributor to move the liquid through the flow distributor, blotting membrane(s) and porous support to the manifold.

IN THE DRAWINGS

Figure 9A:
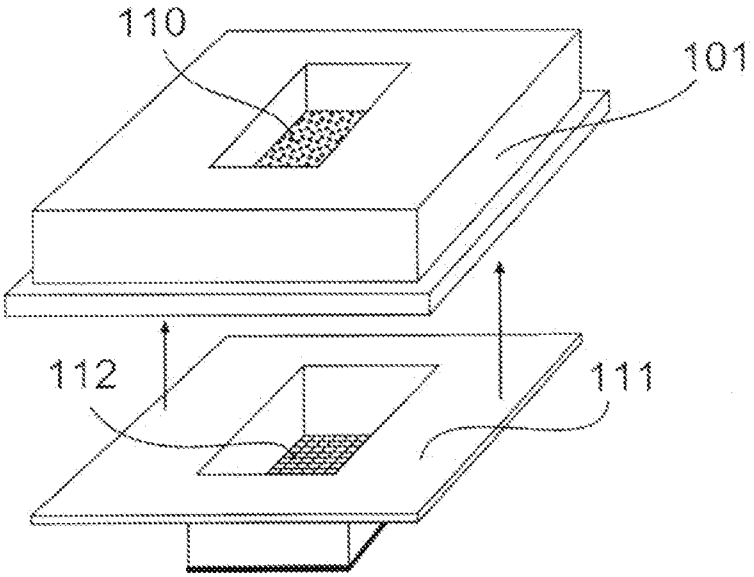

FIGS. 9A and B show another embodiment of the device of the present invention.

Figure 10:
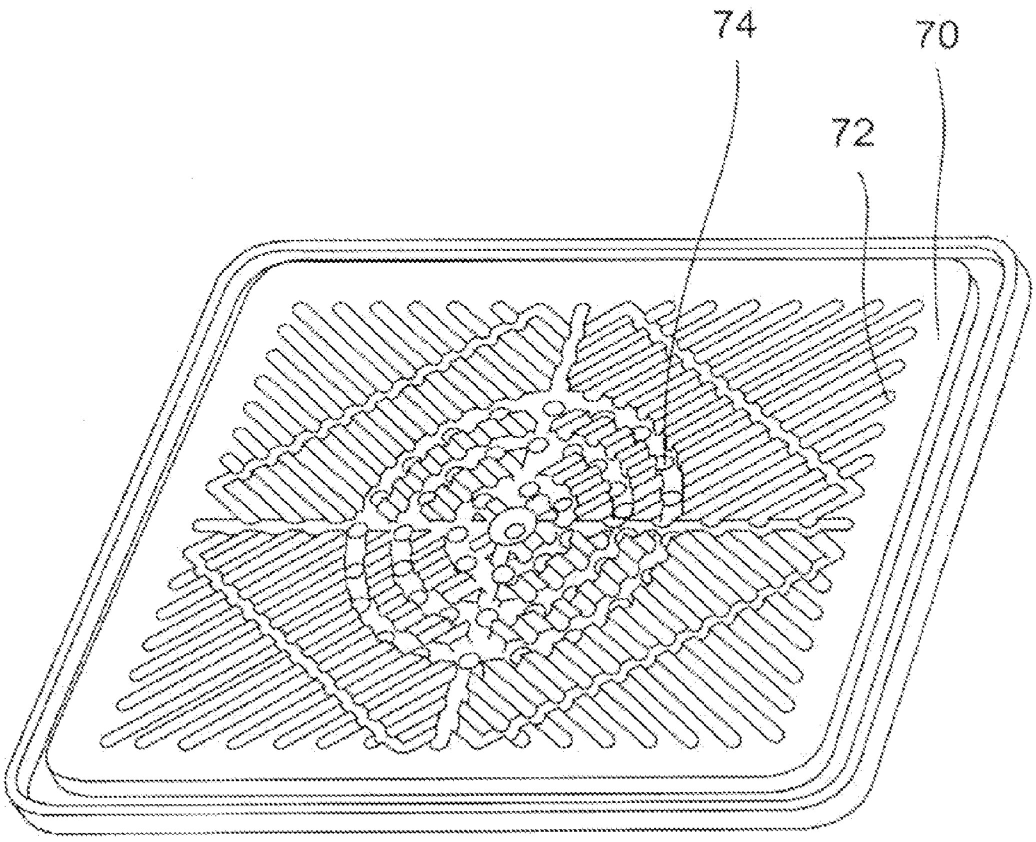

FIG. 10 shows an embodiment of the porous support in perspective view.

Figure 11:
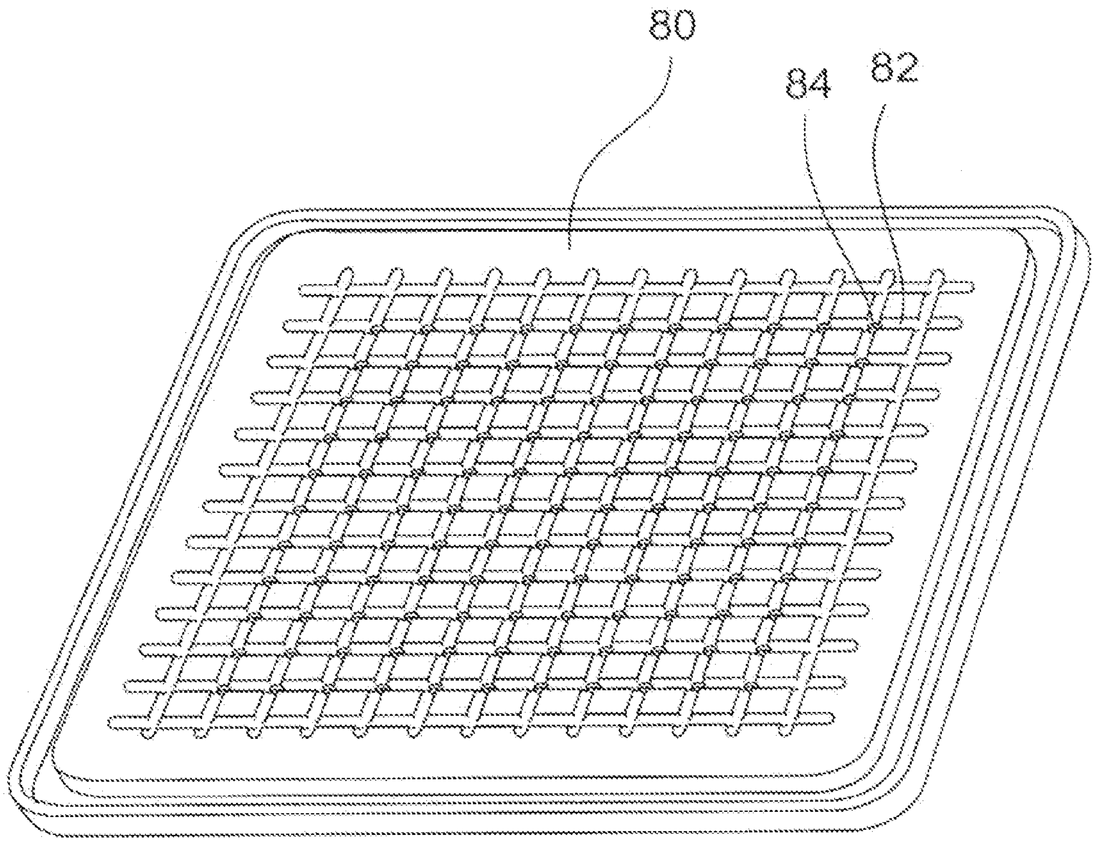

FIG. 11 shows an alternative embodiment of the porous support in perspective view.

Figure 12:
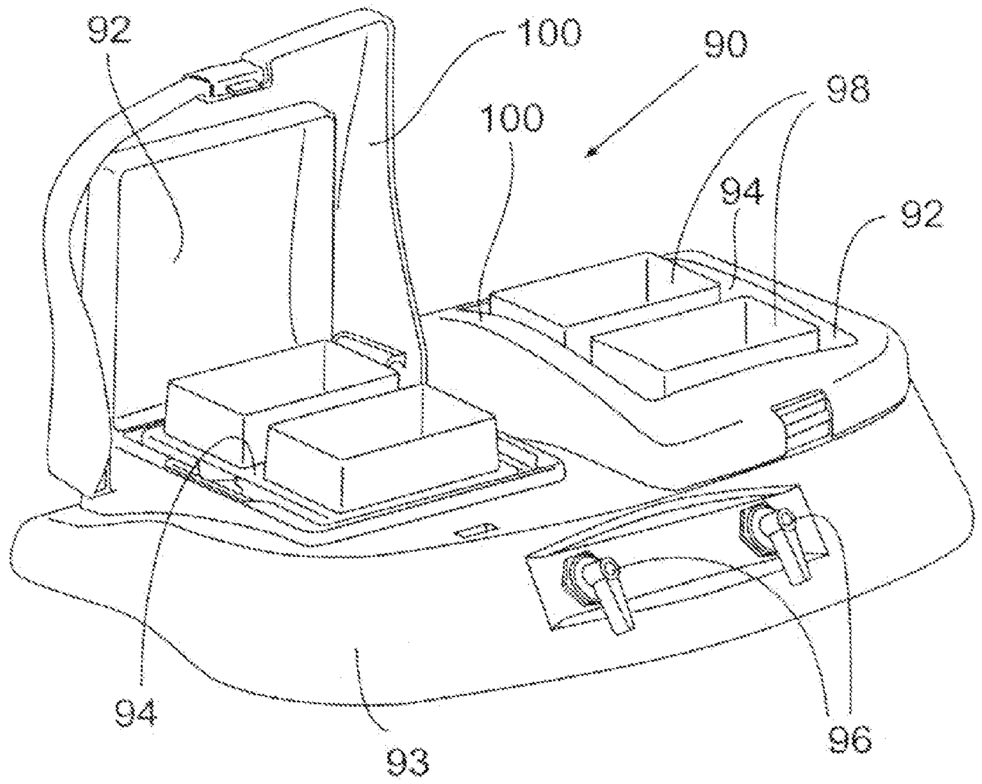

FIG. 12 shows an embodiment of the present invention in perspective view.

DETAILED DESCRIPTION OF THE INVENTION

Figure 1:
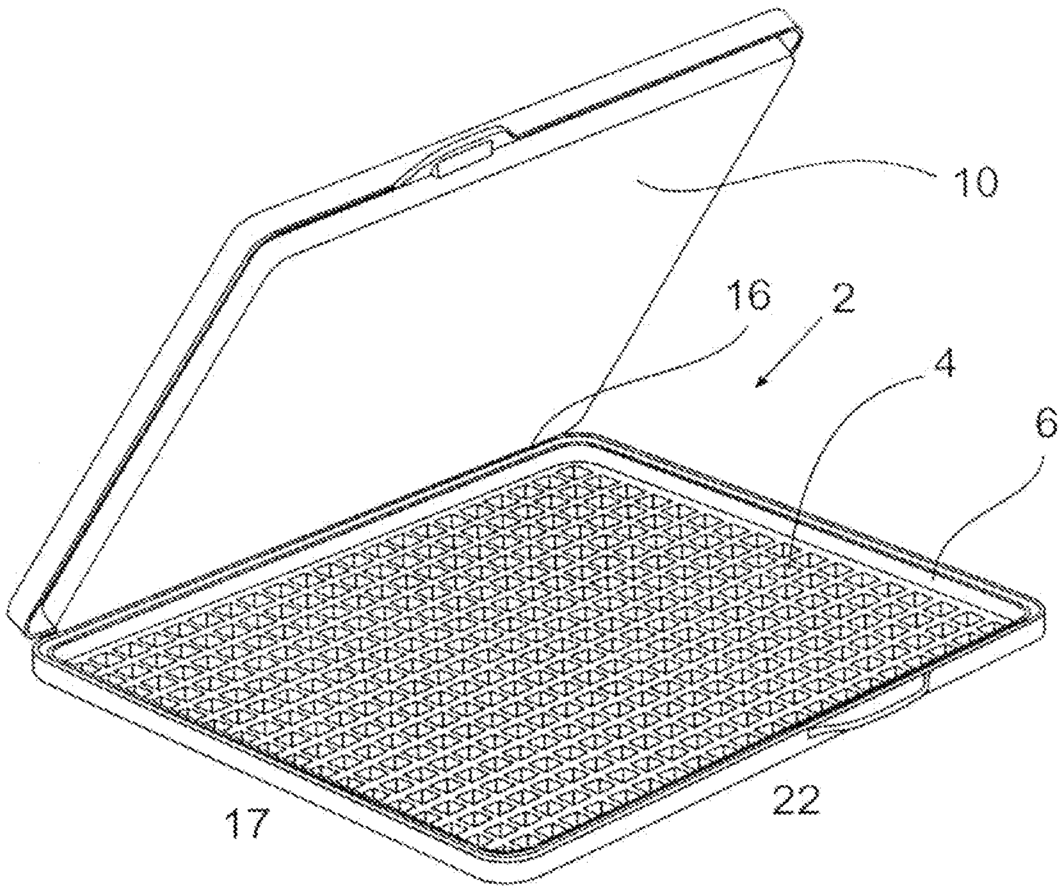
FIG. 1 shows a first embodiment of a device according to the present invention in perspective view.
Figure 3:
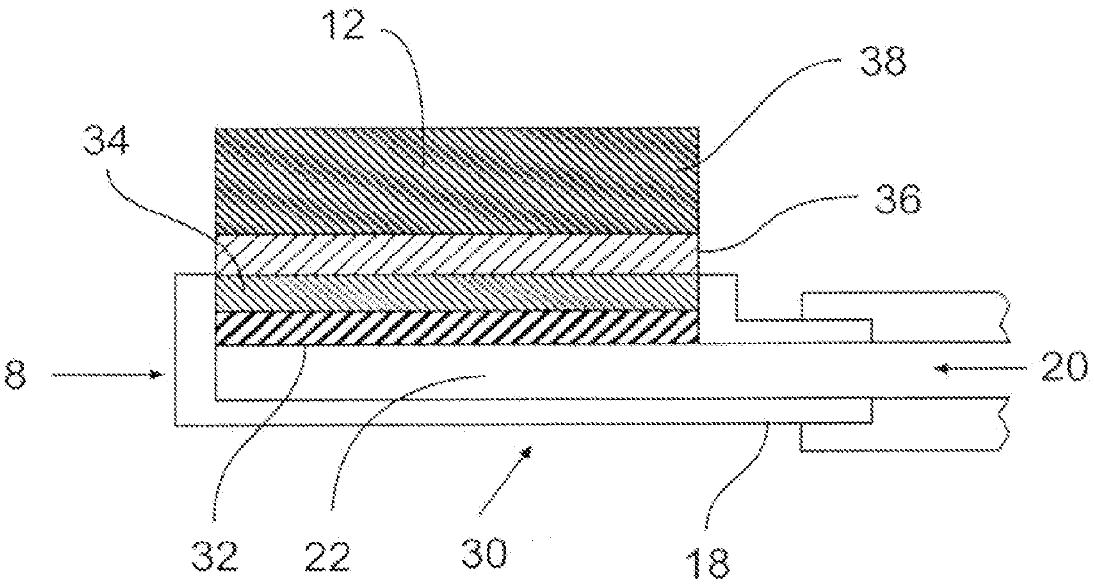
FIG. 3 shows a device according to the present invention mounted in a manifold in cross-sectional view.

As shown in FIG. 1, the holder 2 is comprised of two portions. The first or lower portion is a porous support 4. Preferably the support is formed with an edge 6 or mounting piece that is designed to fit into or onto a manifold 8 (FIG. 3). One or more layers of a blotting membrane (not shown) are placed on top of the support 4 such that the bottom surface of the membrane(s) is in contact with the support's upper surface. The second portion of the holder 2 is a porous flow distributor 10 that is applied against the top of the blotting membrane(s) (not shown).

Figure 2:
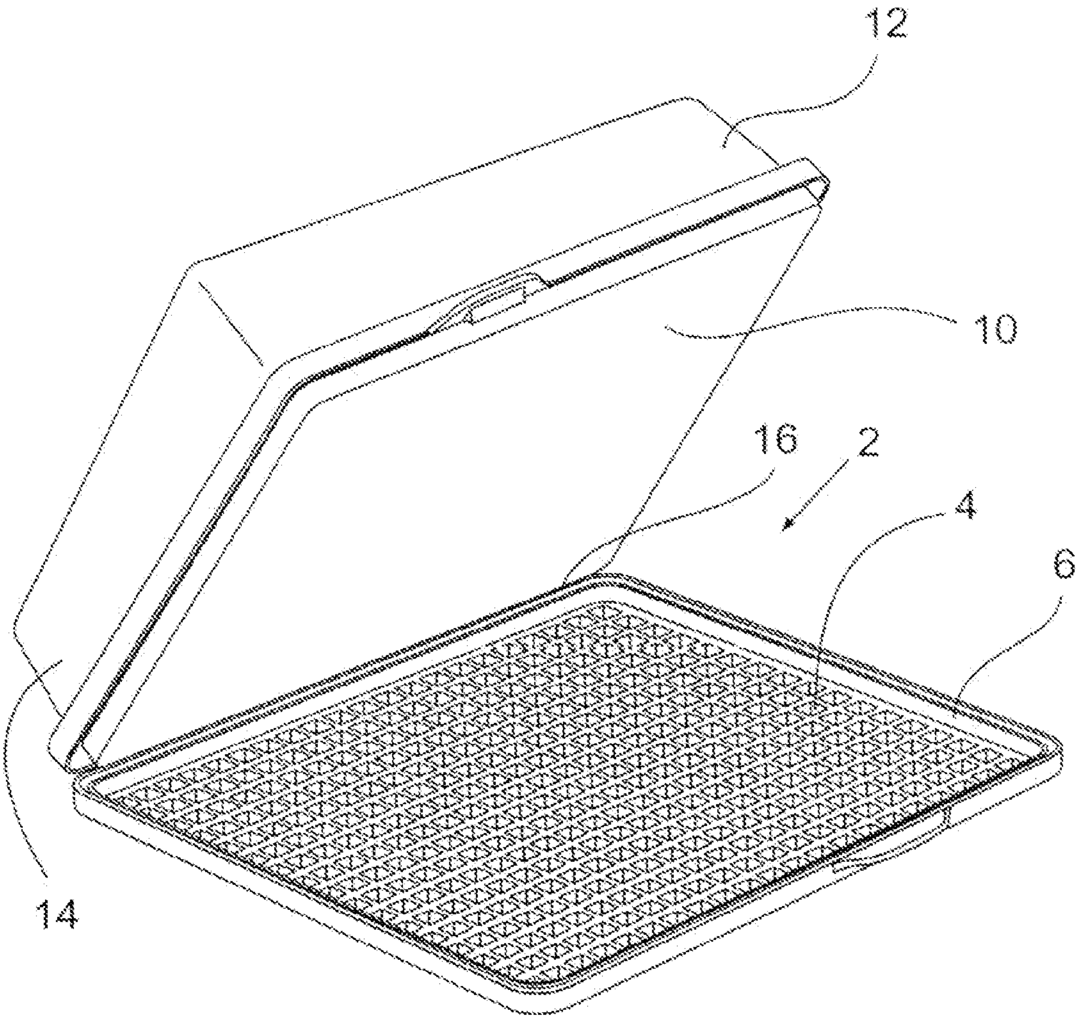
FIG. 2 shows a second embodiment of a device according to the present invention in perspective view.

The top 10 and the bottom 4 pieces are preferably attached to each other at least during use to hold the one or more membranes securely in place. As shown in FIGS. 1 and 2 the two portions 4 and 10 of the holder 2 are held together by a hinge 16. As shown in this embodiment the hinge is a "live" hinge that bonds the two portions together. Alternatively, the hinge could be made separately and attached using adhesives, heat bonds or mechanical fasteners. Other embodiments use no hinge (not shown) and use clips, elastic bands or cooperatively engaging fasteners such as a slot and detent, friction fit pin or the like form on or in the respective top and bottom portions to hold them together during use. Other comparable means will be obvious to one of skill in the art and it is meant to include them as well.

Figure 5:
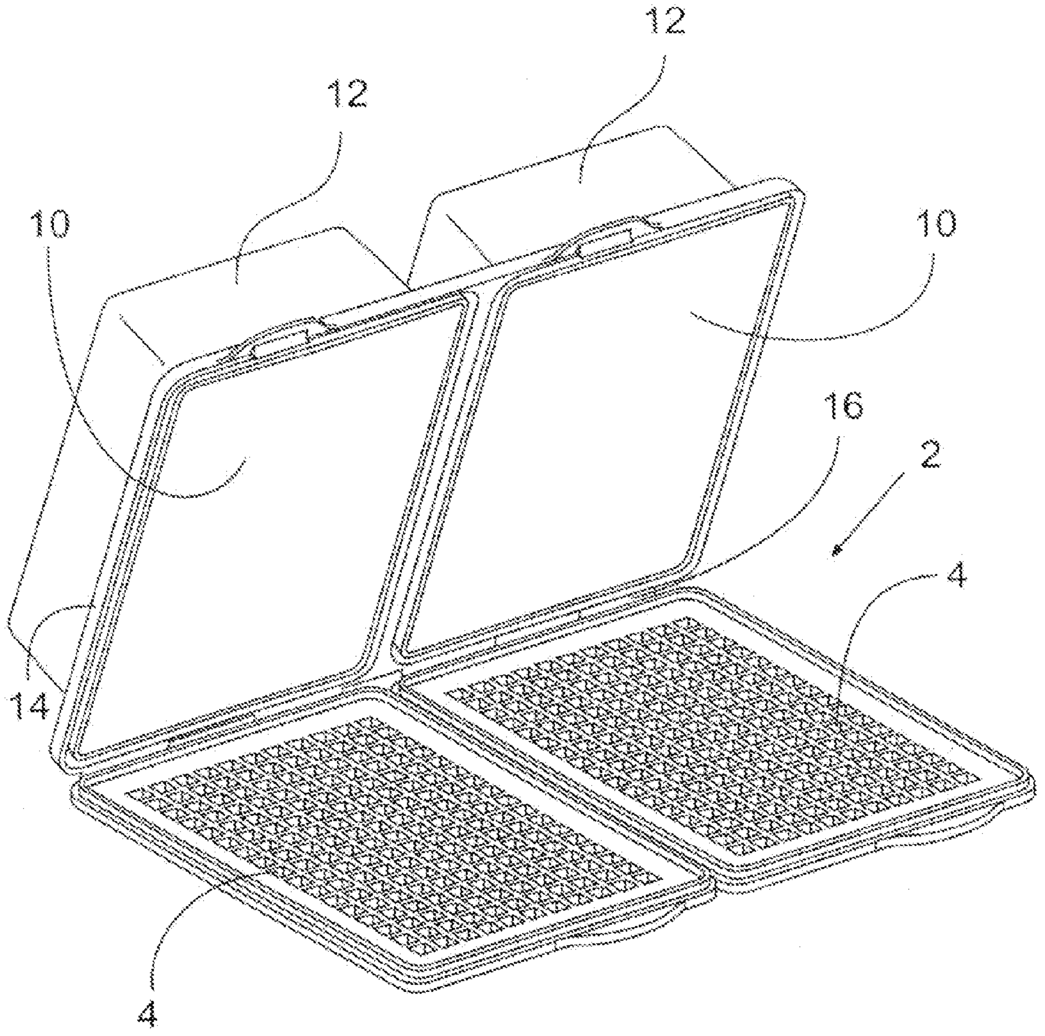
FIG. 5 shows a third embodiment of a device according to the present invention in perspective view.

Optionally and preferably the flow distributor 10 may either have one or more wells 12 for holding washing fluids and reagents during use. In FIG. 5, the holder 2 is shown with two wells 12. The well(s) 12 may either be formed as part of the top surface 14 of the flow distributor 12 (FIG. 2) or as a separate piece 12 (FIG. 3) which is simply attached or placed on top of the flow distributor 10.

Figure 6:
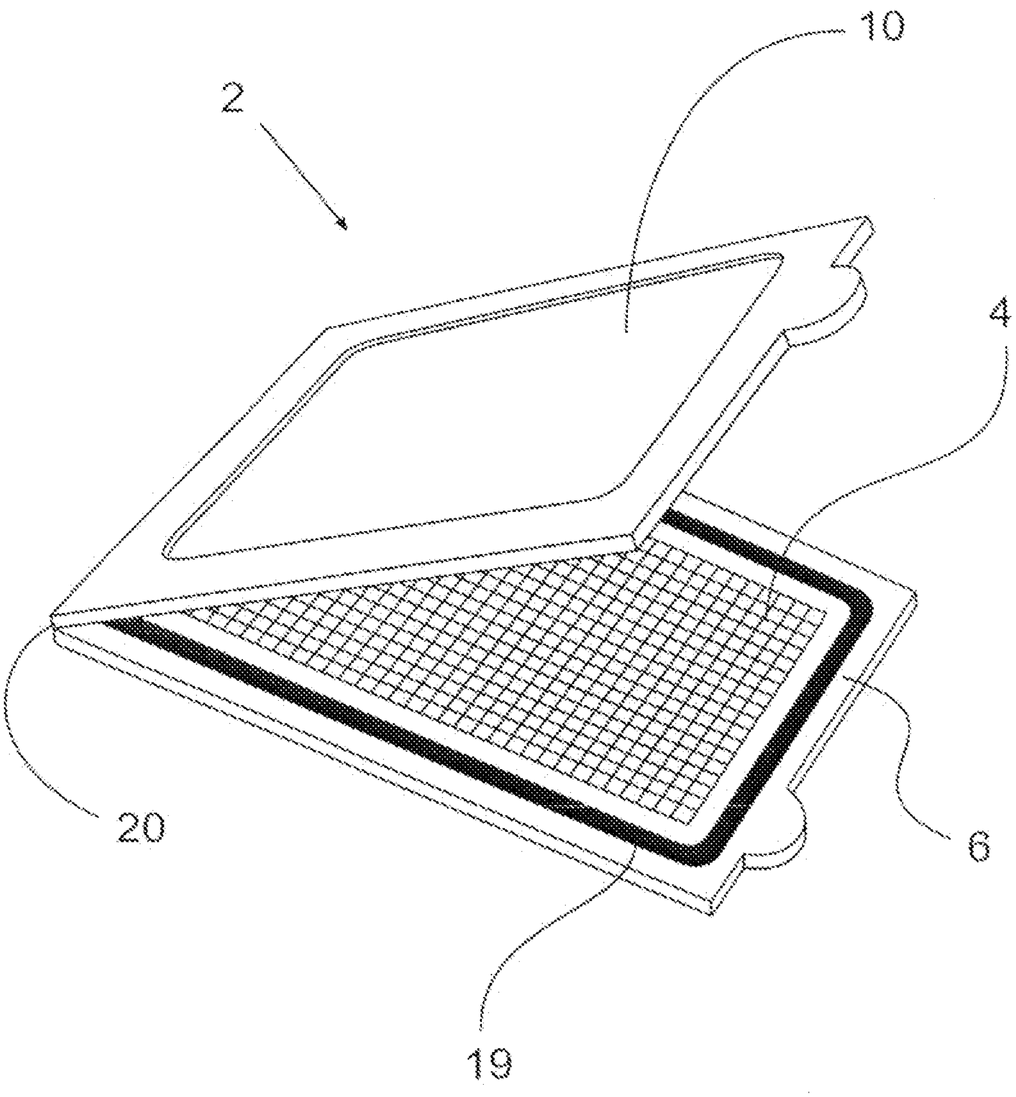
FIG. 6 shows a fourth embodiment of a device according to the present invention in perspective view.

In FIG. 6 is another embodiment of the holder. This is an assembly constructed with thin films such as of plastic or paper. It should be thick enough to be self-supportive and thin enough to be folded. The holder 2 is a film having a thickness from 0.005" to 0.060". The film has a fold line 20 running the width of the holder 2. The film has two openings that are aligned when the holder is folded closed. Covering one opening is the flow distributor membrane 10 and covering the other opening is a porous support 4. Outwardly and circumscribing the porous support opening is a sealing or joining material 19, such as a resealable adhesive. The joining material 19 holds the holder together during handling and use. It would be obvious to one skilled in the art that the holder 2 could be constructed from two films and having a separated material such as an adhesive back film provide the function of the fold line 20.

As shown in FIG. 3, the manifold 8 in this embodiment is a vacuum manifold which has a port 18 that is attached to a source of vacuum 20. Alternatively, positive pressure can be used instead of a vacuum to drive the filtration/washing process by simply placing a pressure hood having a supply of pressurized air or other gas over the top of the holder 2 (In this embodiment, the port 18 simply acts as an outlet for the pressurized air/gas.) The port 18 is located below the porous support 32. A waste collection device 22, in this instance, a receptacle, is mounted below the manifold or if desired in the manifold (not shown) to collect the liquid pulled through the device 2.

Figure 8:
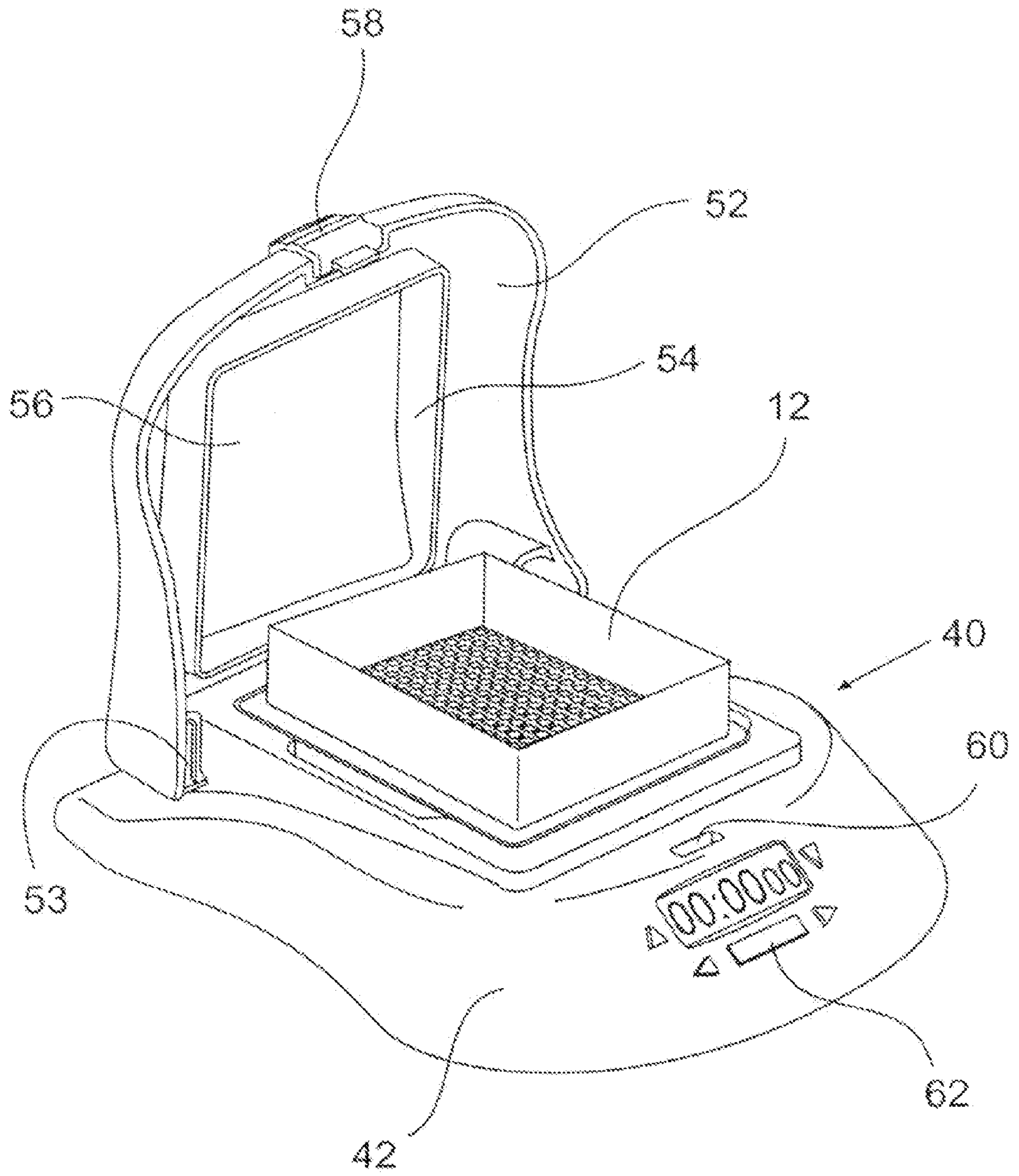
FIG. 8 shows a preferred embodiment of a device in a manifold according to the present invention in perspective view.

Alternatively, the waste collection device 22 can be a waste drain or other similar device as is known to one of ordinary skill in the art. In this instance the holder 2 is formed of a porous support structure 32, such as a plastic or metal grid or a porous sintered sheet of plastic or metal or other similar devices as are well known in the art. The one or more blotting membranes 34 is again placed on top of the support 32, over which is the flow distributor 36 and a well structure 38 (if desired) as described above in relation to the embodiments of FIG. 2. FIG. 8 shows the holder of FIG. 2 mounted on a manifold described below in relation to FIG. 4.

Figure 4:
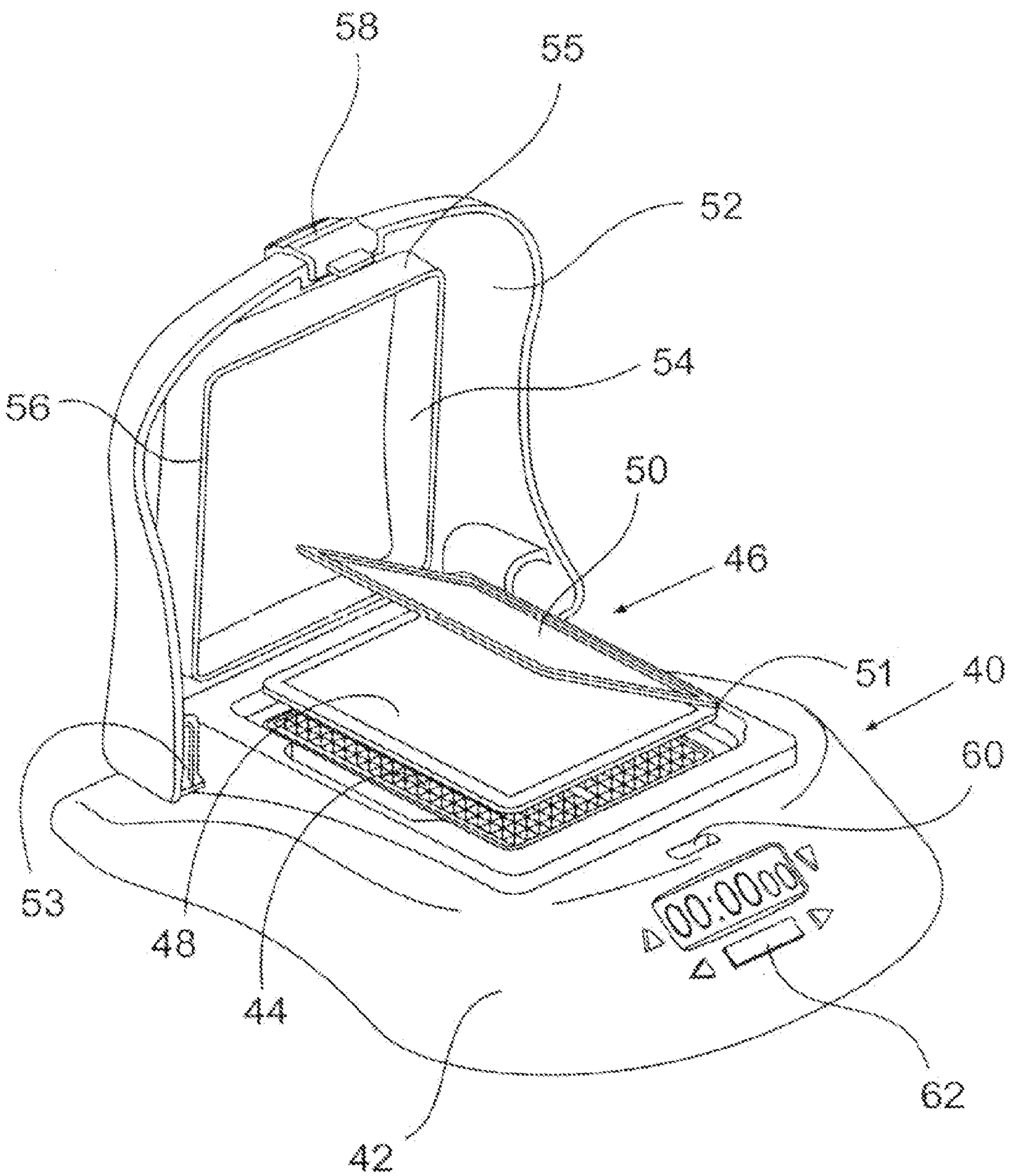
FIG. 4 shows an embodiment of the device in a manifold according to the present invention in perspective view.

FIG. 4 shows a preferred form of a manifold 40. The manifold has a base 42, having a drain and support surface 44 on which the holder 46 (formed of the lower support 48 and the upper flow distributor 50) is placed. As shown the holder uses a hinge 51 to hold the upper and lower portions to each other. One or More membranes are inserted between the lower and upper portions of the holder 46 which is then closed. Attached to the base 42 is a removable cover 52. In this embodiment the cover 52 is attached to the base 42 by pivot points 53 (one shown) so that it can open and close upwardly and rotationally respective to the base 42. A separate well 54 may be mounted in an opening 55 in the cover 52. Preferably as shown, the bottom portion of the well 54 has an outwardly extending base or lip 56 that holds the well 54 in the opening 55. Additionally, the well 54 can be dimensioned such that there is a slight friction fit between it 54 and the opening 55 to also keep it in place. The cover 52 also has a device such as the clip 58 that mated with a detent 60 on the base 42 so that it can secure the lid 52 to the base 42 when the lid 54 is rotated into a closed position against the base 42. Also shown are the optional controls 62 for managing and monitoring the manifold 40 and the process. The device can be used with automated liquid handlers and the like if desired.

In an additional embodiment as shown in FIG. 12, the manifold 90 can process more than one holder 94. The base 93 can be designed with multiple stations 92 to position multiple holders 94. Also as shown in this embodiment the holder 94 in each station 92 can be subdivided into two or more wells 98 if desired. The manifold 90 can have a common pressure source or each station 92 can be pressure controlled individually such as by control knobs 96 as shown. The cover 100 can close on all the holders or as in this embodiment can have a separate cover for each station 92. This format minimizes the laboratory bench space used for the higher through put laboratories.

The flow distributor 10 is a porous structure. The flow distributor not only provides even liquid distribution but it also acts as a flow regulator. It provides for complete and uniform distribution of the liquids as well as allowing sufficient time residence in the membrane for proper interaction between the molecules of the liquid and the specimen. In one embodiment, the entire structure is porous. In another embodiment, such as may be used in conjuncture with the embodiment of FIG. 2, the flow distributor 10 is only porous in the area within the well(s) 12. The area 16 of the distributor 10 that is non-porous can be rendered so by filling the pores in that area 16 with a non-porous material such as a plastic or a glue, by collapsing the pores in that area 16 with heat and/or pressure and/or solvents as is well known in the art or by forming the distributor 10 to match the size of the outer dimension of the well(s) 12 and liquid tightly sealing the distributor 10 to the bottom of the well(s) 10 along its outer dimension (as shown in FIG. 2).

The flow distributor 10 may be any porous structure that provides for even distribution of the liquid across its face and which is sufficiently porous to allow for easy movement under the influence of a vacuum or pressure and which is also capable of filtering out agglomerates, particles and other debris from the liquid.

The flow distributor may be of any desired size. Gels come in a variety of "standard" sizes from about 7 cm by 8 cm to a 20 cm by 20 cm area. The flow distributor should preferably cover the entire blotting membrane to insure complete flow of reagents through all of the blotting membrane.

Such materials include but are not limited to woven, non-woven and fibrous porous filters such as TYVEK® or TYPAR® paper, cellulosic materials such as MF filters available from Millipore Corporation of Billerica, Mass., membranes such as DURAPORE® and MILLIPORE EXPRESS® microporous membranes available from Millipore Corporation of Billerica, Mass., sintered membranes such as POREX® filters and the like. Preferred are membranes, especially plastic microporous membranes.

A preferred pore size of such membranes is between about 0.1 and about 0.65 micrometer, preferably between 0.2 and about 0.45 micrometer and more preferably about 0.22 micrometer.

Additionally, the preferred porous structure has low binding characteristics for the reagents used in order to minimize the amount used. More preferably, as it is generally used with biological materials it is hydrophilic and has low protein binding characteristics. One such distributor is a hydrophilic DURAPORE® membrane formed of PVDF available from Millipore Corporation of Billerica, Mass. Another is a MILLIPORE EXPRESS® hydrophilic PES membrane available from Millipore Corporation of Billerica, Mass.

The porous support 4 may be a simple screen, a grid (as shown in FIGS. 1 and 2), a flow directing grid or a sintered porous structure such as a POREX® membrane or a coarse or large pored microporous filter, such as a woven or non-woven paper, a polypropylene or polyethylene fabric, a glass mat or paper, or a 1-10 micron microporous filter. Such supports can be made of polymer, glass, ceramic or metal materials including but not limited to metals, such as stainless steel or steel alloy, aluminum and the like, and polymers such as polyethylene, polypropylene, polysulfone, polyethersulfones, styrenes, nylons and the like.

FIG. 10 shows a porous support in the form of a flow directing grid 70 consisting of a series of grooves 72 and openings 74. The openings 74 are inwardly positioned from the perimeter of the porous support 70. The openings 74 are in fluid communication with the grooves 72 so that fluid is collected in the grooves 72 and directed through the openings 74. The grooves 72 collect and deliver the spent fluid to the openings 74 which direct the fluid to a waste chamber or the collection tray in the holder (manifiold) (not shown). If the researcher wishes to collect one or more of the fluids, then a collection tray can be positioned inside the manifold below the openings 74 to collect the spent fluids. FIG. 11 is an additional embodiment of the grid 80 for directing spent fluids into grooves 82 and out the openings 84. This embodiment consist of a series of rectangular grooves 82, it would be obvious to use other designs for grooves 72 or 82 and openings 74 or 84. The desired outcome is to direct the spent fluids to an opening or a series of openings that direct the spent fluids to a collection tray.

The outer edges of the support 4 and the flow distributor 10 may be made of the same materials as the support 4. When an integral hinge is used, it must be made of a flexible material such as polyethylene, polypropylene, an elastomer or one of the impact modified materials such as ABS, K-resin and the like. When a separate hinge, clips, elastic bands, adhesive film or other securing means are used they may be made of metal, plastic or elastomers as desired.

Figure 9B:
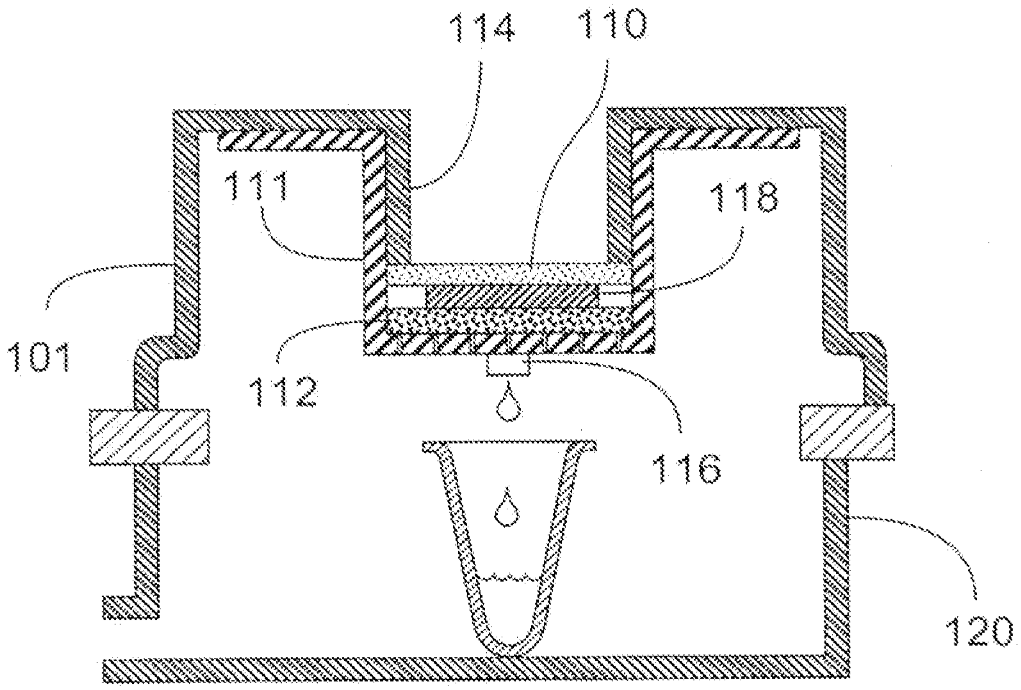

FIGS. 9A and 9B show another embodiment of the present invention in which the flow distributor 110 is in the form of a single (as shown) or preferably multiple well format 101 The support 112 is formed as a separate piece 111 that attaches to the wall(s) of the well(s) 114 of the distributor 110. This may be a friction fit or preferably a snap fit to releasably retain the structure together during use. Alternatively adhesives such as adhesive pads (not shown) can be mounted to the bottom side of the distributor 110 or the top surface of the piece 111 containing the support 112 to hold them together. A grid with a spout 116 is located at the bottom of the piece 111 that contains the support 112. A membrane 118 is laid on top of the support 112 which then attached to the flow distributor 110. The welled device 101 is then placed on or in a pressure or vacuum manifold 120 with a collection device such as a waste tray or a multiwell plate or a series of one or more tubes (as shown) to collect fluid that is moved through the system.

Various methods may be used in the present invention. The key factor being that they all rely on a vacuum or positive pressure driven filtration of the liquids to access the large inner surface area of the membrane allowing 3-D interaction of all the molecules throughout the depth rather than only 2-D interaction at the surface as has occurred in the past.

The simplest method is to use the present invention to conduct one or more of the washing cycles. Typically each washing cycle is comprised of one or more washing steps. Generally, 2-5 steps are used per cycle.

Another method is to use the present invention in each step in which liquid needs to be moved through the blotting membrane such as after incubation of the antibodies or in the washing steps.

In all of these processes, any pressure suitable to move the liquid(s) through the device and into the manifold can be used. This can vary depending upon the membranes selected for blotting and the flow distributor, the manifold used, the desired speed of the filtration and the supply of vacuum or positive pressure available to the researcher.

Generally, the vacuum available may vary between 100 and 760 mm Hg (133 millibars and 1013 millibars). The use of valves, pressure restrictors and the like may also be used to keep the vacuum within the allowed ranges for the membranes used. A preferred vacuum manifold of one embodiment of the present invention uses of a vacuum of about 100 mm Hg. Other suitable vacuum manifolds include but are not limited to the MULTISCREEN™ and MULTISCREEN™ $_{HTS}$ vacuum manifolds available from Millipore Corporation of Billerica, Mass.

Generally the positive pressure is supplied by an air line at pressures ranging from about 2 psi to about 15 psi. The use of valves, pressure restrictors and the like may also be used to keep the pressure within the allowed ranges for the membranes used. Such pressure systems include but are not limited to Amicon® stirred cell devices available from Millipore Corporation of Billerica. Mass. and positive pressure filtration units available from Caliper Life Sciences of Hopkinton, Mass.

To use a device according to the invention one simply takes a holder, opens it and places the blotting membrane(s) on one of the surfaces such that the lower surface of the blotting membrane is adjacent the porous support and the upper surface of the blotting membrane is adjacent the flow distributor when the device is closed around the membrane(s) so as to have no air bubbles between the blot and the flow distributor. Bubbles between these two surfaces can cause areas of no flow. The device is placed on or in a manifold having a pressure supply (vacuum or positive pressure). Preferably the blotting membrane(s) has been prewet. The pressure (vacuum or positive pressure) is turned on and a liquid, such as a wash liquid or a reagent, is placed on top of the flow distributor or into the well(s) if used. The pressure continues until the liquid has been moved through the device and membrane(s). Then the pressure is turned off.

When more than one blotting membrane is used, they can be arranged in series on top of each other and sufficient liquid containing the same desired reagents can be easily moved through the multiple layers in one process step. Generally when more than one layer is used it is preferred that one use between 2 and 10 layers, preferably between 2 and 5 layers at a time. Alternatively, one can use a flow distributor having multiple subwells and use more than one blotting membrane in parallel to each other, each with their own well in the flow distributor and each with its own set of reagents as is required for its specific purpose. Also one can mount two or more separate holders each with one or more subwells. One can even use multiple layers in adjacent wells if desired. With two or more separate holders, they may if desired be run independently of each other or together.

The liquid can either be added with the pressure supply being off or the supply being turned on only briefly so as to get the liquid into the membrane(s) and is allowed to incubate (such as may be required with the primary or secondary antibodies). The pressure is then turned on to remove the liquid and/or replace it with another used sequentially. Preferably, during washes, the vacuum is left on and remaining washes are added sequentially.

Figure 7:
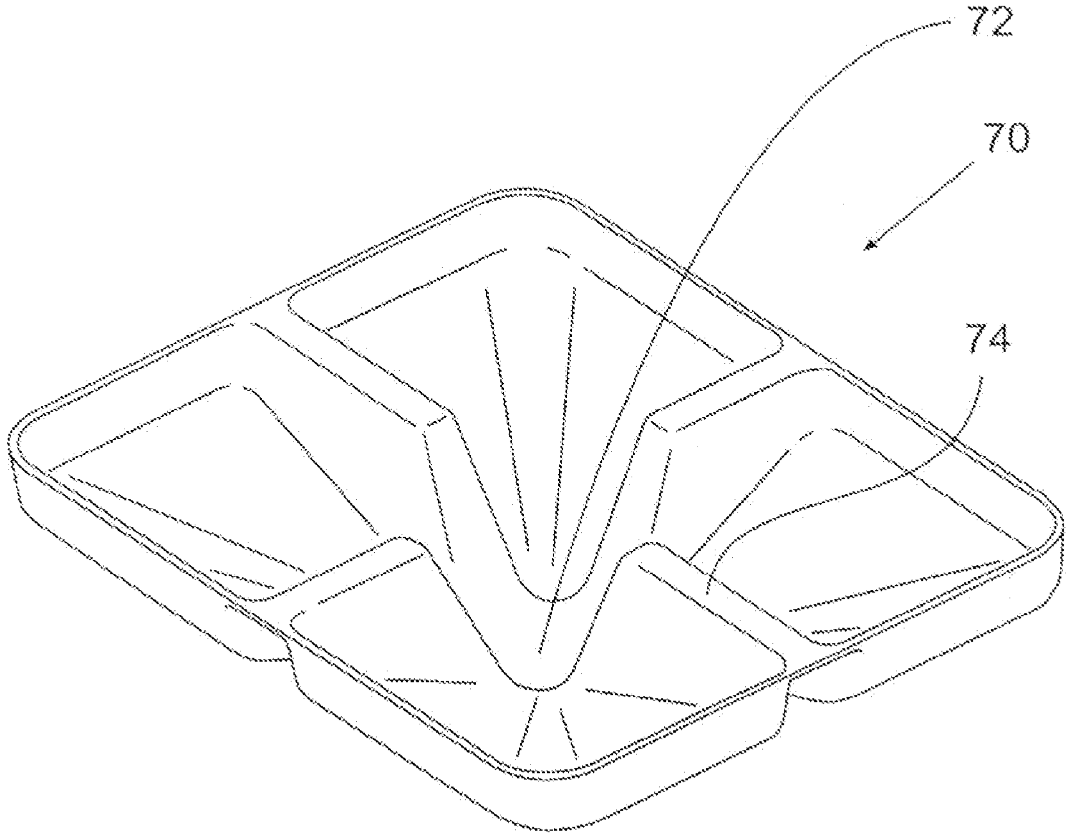
FIG. 7 shows an embodiment of a reagent collection device according to the present invention in perspective view.

Optionally, if one wishes, one can place a collection vessel 70 below the device, preferably in the manifold itself or downstream. It can then be used to collect one or more unbound reagents that may be expensive and which can be collected and recycled for use in future assays. The vessel can also be subdivided into multiple chambers that are in alignment and fluid communication with the respective portion of the blotting membrane. One such collection vessel 70 is shown in FIG. 7, with a central collection point 72 and support ribs 74 to mate with the downstream surface of the support 4. Other embodiments can also be used.

Additionally or alternatively, one can place in the downstream flow path below the holder an absorbent matrix that is capable of reversibly binding one or more unbound reagents that are expensive. The matrix is preferably in the form of a monolith, such as a pad, a plug or a paper sheet, that is positioned so that all the liquid passing through the blotting membrane and holder passes through the matrix. It can then either be removed and the reagent eluted or if desired, it can have the bound reagents eluted in situ after completion of the testing of the blotting membrane.

Other processes may also be used with the device of the present invention. The membrane contains, in its interstices, one or more substances to be detected. Generally these substances are present in the interstices either by virtue of having been blotted from a solid support for electrophoresis or chromatography or by direct application, usually to detect the presence, absence, or amount of a particular type of material such as an antibody or specific protein—i.e. a Dot-Blot type assay as described above. The definition of the membrane is not limited, however, to these instances, but applies to any case wherein a membrane contains in its interstices one or more substances to be detected. Included in the types of membranes envisioned for use in the present invention are membranes commonly used to blot electrophoresis gels such as nitrocellulose; nylon; or various other polymeric membranes, such as polyvinylidene fluoride (PVDF), sold as IMMOBILON™ membranes by Millipore Corporation of Billerica, Mass.

A variety of materials can be used to replicate the results of electrophoresis gels performed on various samples as is understood in the art. Most commonly, the samples contain biological substances such as individual proteins, antibodies, nucleic acids, oligonucleotides, complex carbohydrates, and the like, but the application of the technique is not limited to these substances. The invention technique is applicable to any membrane containing within it a substance to be detected regardless of the chemical composition of the membrane or of the target substances.

When membranes which represent replicas of electrophoretic results are employed, the transfer of the substances to be detected from the gel to the membrane can be conducted by utilizing membranes containing transfer buffer, by electroelution, or by dry blotting of the gels. Techniques for these transfers are well understood in the art, and do not constitute part of the invention herein.

The liquid to be supplied may contain detecting reagents or may simply be provided as a wash. The nature of the detecting reagent depends, of course, on the substance to be detected. Typically, proteins are detected by immunological reactions between antigen and antibody or immunoreactive portions thereof; typically the presence of nucleic acid fragments is detected by suitable oligonucleotide probes. The detecting substances responsible for the immediate or specific reaction with the substance to be detected may be further supplemented, if needed, with label and a multiplicity of applications of the detecting reagents may be needed—e.g., a protocol may include detection of an antigen by supplying an antibody labeled with an enzyme, e.g., commonly, horseradish peroxidase, and then this binding is detected by means of supplying substrate for this enzyme. In application of reagent, it is possible, though not preferred, to use only a positively pressed donor matrix to expose this component of the membrane for a defined period.

It is most convenient to conduct the method of the invention at room temperature, but elevated and lower temperatures can also be used. This can be effected by heating the device, its surrounding environment (as in a heat box or cooling box) or the liquids used in the system.

Blots can be sequentially analyzed with multiple antibodies or probes in the present device and process by stripping the previously bound antibodies from the blot followed by subsequent incubations with antibodies or other probes specific other target proteins. The stripping process disrupts the antigen-antibody bonds and dissolves the antibodies in the surrounding buffer. This is usually achieved by a combination of detergent and heat or by exposure to either high or low pH. The device, in combination with the flow distributor, enables the stripping of blots using the high or low pH method. The subsequent reprobing of blots either directly (e.g., using the same flow distributor used for striping) or subsequently after storage, would use the same protocol as the initial probing. Suitable kits for strip blotting are available from Chemicon International, Inc under the brand names of ReBlot™ Plus kit (catalogue # 2500), ReBlot Plus-Mild solution (catalogue # 2502) and ReBlot Plus-Strong solution (catalogue #2504).

In standard western blotting, the antigen or target is transferred to a membrane support and probed with a suitable probe such as an antibody, protein (e.g., Protein A) or lectin (proteins or glycoproteins which binding to carbohydrate moieties). In some applications, a reverse format (e.g., reverse array) is used, wherein the antibody or other probes are spotted onto a membrane or other support (typically in an array format) and the antigen or target is presented to the immobilized antibodies on the array. Visualization of a target-probe binding event can be achieved by labeling of the antigens or targets or by using a secondary antibody specific for the target. Reverse arrays often employ mixtures of targets, for example lysates labeled with different fluorescent colors to enable parallel processing. Reverse assays can also be performed with the present invention.

What we claim:

1. A device for conducting immunoassays comprising a holder formed of the holder having a first portion and second portion, a central opening area formed in each of the first and second portion, the opening of each portion being aligned with the other opening of the opposite portion when the first portion and second portions of the holder are adjacent each other in a closed position, wherein the holder is formed of a single piece of paper and the first and second portions are delineated by a fold line running the width of the material between the first and second portions, a porous support covers opening of the first portion and a flow distributor covers the opening of the second portion wherein the flow distributor is a hydrophilic membrane and the holder has a means for releasably securing the first and second portions to each other.

2. The device of claim 1 wherein the flow distributor has a lower and an upper surface and the second portion of the holder has an inner and outer surface and the flow distributor is attached to the inner surface of the second portion of the holder such that the thickness of the second portion from the inner surface to the outer surface forms one or more wells above the flow distributor.

3. The device of claim 1 further comprising a collection tray below the holder for the recovery of reagents.

4. The device of claim 1 further comprising a collection tray below the holder for the recovery of reagents and wherein the tray is subdivided into two or more separate subtrays.

5. A device for conducting vacuum assisted immunoassays comprising a vacuum manifold and a holder formed of a material selected from the group consisting of plastic film and paper, the holder having a first portion and second portion, a central opening area formed in each of the first and second portion the opening of each portion being aligned with the other opening of the opposite portion when the first portion and second portions of the holder are adjacent each other in a closed position, wherein the holder is formed of a single piece of material selected from the group consisting of plastic film and paper and the first and second portions are delineated by a fold line running the width of the material between the first and second portions, a porous support covers opening of the first portion and a flow distributor covers the opening of the second portion wherein the flow distributor is a hydrophilic membrane and the holder has a means for releasably securing the first and second portions to each other.

6. The device of claim 5 wherein the flow distributor has a lower and an upper surface and the second portion of the holder has an inner and outer surface and the flow distributor is attached to the inner surface of the second portion of the holder such that the thickness of the first portion from the inner surface to the outer surface forms one or more wells above the upper surface of the flow distributor.

7. The device of cairn 5 wherein there are two holders which are run independently of each other.

8. The device of claim 5 wherein the holder is formed of paper.

9. The device of claim 5 wherein the holder is formed of plastic film.

10. A device for conducting immunoassays comprising a holder formed of a material selected from the group consisting of plastic film and paper, the holder having a first portion and second portion, a central opening area formed in each of the first and second portion, the opening of each portion being aligned with the other opening of the opposite portion when the first portion and second portions of the holder are adjacent each other in a closed position, a porous support covers opening of the first portion and a flow distributor covers the opening of the second portion wherein the flow distributor is a hydrophilic membrane and the holder has a means for releasably securing the first and second portions to each other and the holder is formed of a single sheet of material and the first and second portions are delineated by a fold line running the width of the material between the first and second portions.

11. The device of claim 10 wherein the holder is formed of plastic film.

12. The device of claim 10 wherein the material of the holder is paper.

* * * * *